United States Patent
Huet

(10) Patent No.: US 7,867,201 B2
(45) Date of Patent: Jan. 11, 2011

(54) ANTI-STICK DEVICE FOR BENT INJECTION NEEDLE

(75) Inventor: Jean-Max Huet, Clichy (FR)

(73) Assignee: Vygon, Ecouen (FR)

( * ) Notice: Subject to any disclaimer, the term of this patent is extended or adjusted under 35 U.S.C. 154(b) by 1018 days.

(21) Appl. No.: 10/562,334

(22) PCT Filed: Nov. 20, 2003

(86) PCT No.: PCT/FR03/03435

§ 371 (c)(1),
(2), (4) Date: May 12, 2005

(87) PCT Pub. No.: WO2004/047889

PCT Pub. Date: Jun. 10, 2004

(65) Prior Publication Data

US 2006/0161109 A1    Jul. 20, 2006

(30) Foreign Application Priority Data

Nov. 21, 2002   (FR) .................................. 02 14578

(51) Int. Cl.
*A61M 25/00* (2006.01)
(52) U.S. Cl. ..................... 604/177; 604/192; 604/162
(58) Field of Classification Search ................ 604/116, 604/174, 180, 110, 263, 93.01, 198, 177, 604/192, 162
See application file for complete search history.

(56) References Cited

U.S. PATENT DOCUMENTS

| | | | | | |
|---|---|---|---|---|---|
| 3,538,915 | A | * | 11/1970 | Frampton et al. | 604/272 |
| 4,579,120 | A | * | 4/1986 | MacGregor | 600/392 |
| 5,116,324 | A | * | 5/1992 | Brierley et al. | 604/180 |
| 5,238,010 | A | * | 8/1993 | Grabenkort et al. | 128/888 |
| 5,531,704 | A | * | 7/1996 | Knotek | 604/192 |
| 5,951,522 | A | * | 9/1999 | Rosato et al. | 604/177 |
| 6,663,604 | B1 | * | 12/2003 | Huet | 604/263 |
| 6,755,805 | B1 | * | 6/2004 | Reid | 604/110 |

FOREIGN PATENT DOCUMENTS

EP   1116493 A1 *  7/2001

\* cited by examiner

*Primary Examiner* — Nicholas D Lucchesi
*Assistant Examiner* — Laura A Bouchelle
(74) *Attorney, Agent, or Firm* — Levine & Mandelbaum

(57) ABSTRACT

The invention concerns an anti-stick device for a bent injection needle.

The device is composed of a wall formed by articulated panels (1, 2, 3) including a base panel (1), a needle-holding panel (2), and a covering panel (3). The base panel (1) has two opposite lateral branches (1b, 1d) which are pre-curved to facilitate their application on the skin, and two other opposite lateral branches (1c, 1e) capable of being bent at will for pressing them onto the skin. The two other panels have curvatures to match the curvature of the pre-curved branches when they are folded down onto the base panel.

Application to feeding an implanted chamber.

7 Claims, 5 Drawing Sheets

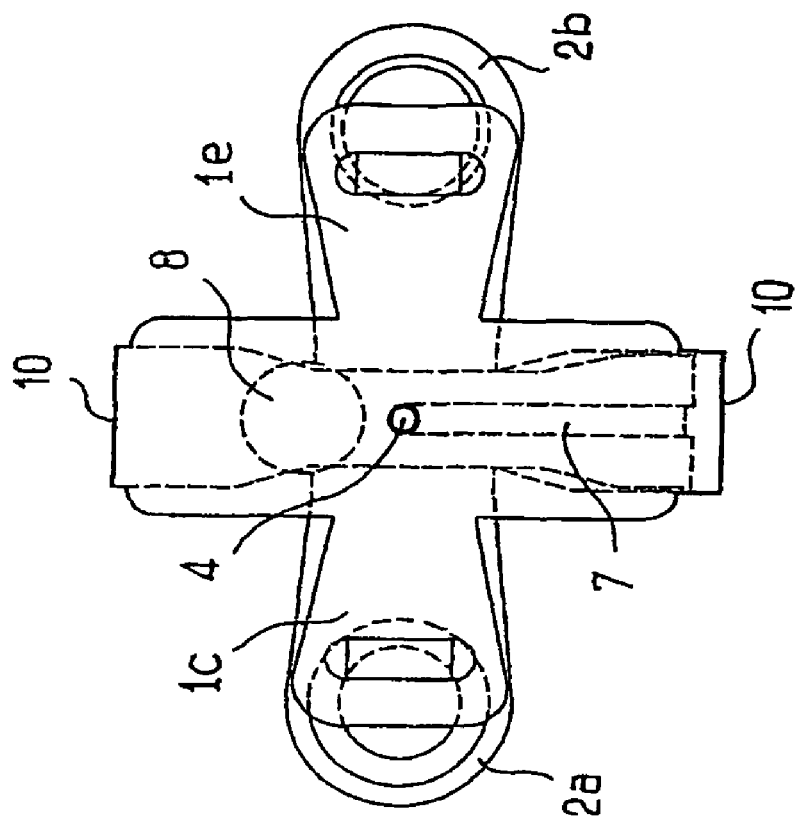
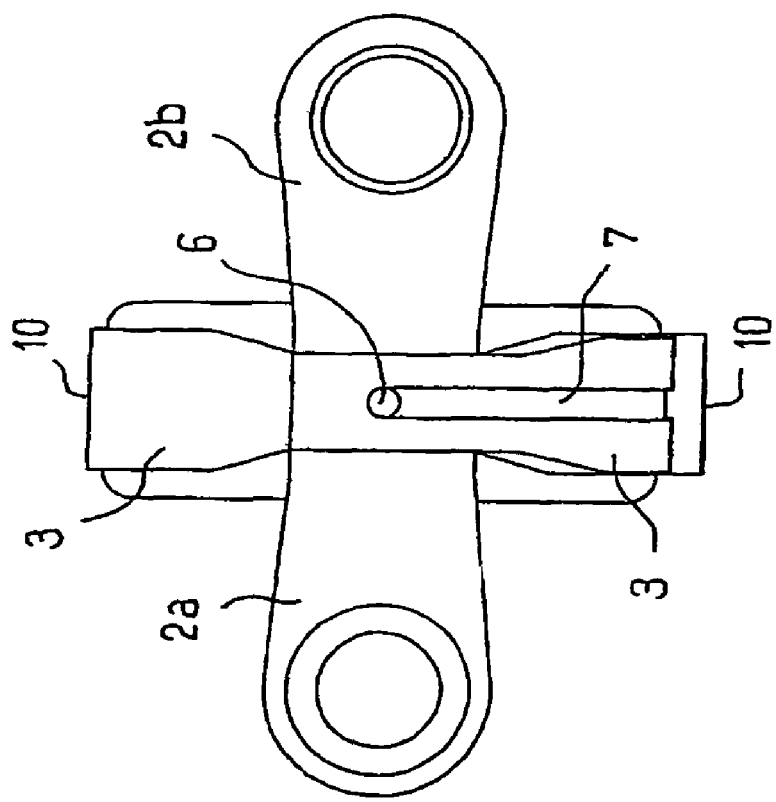

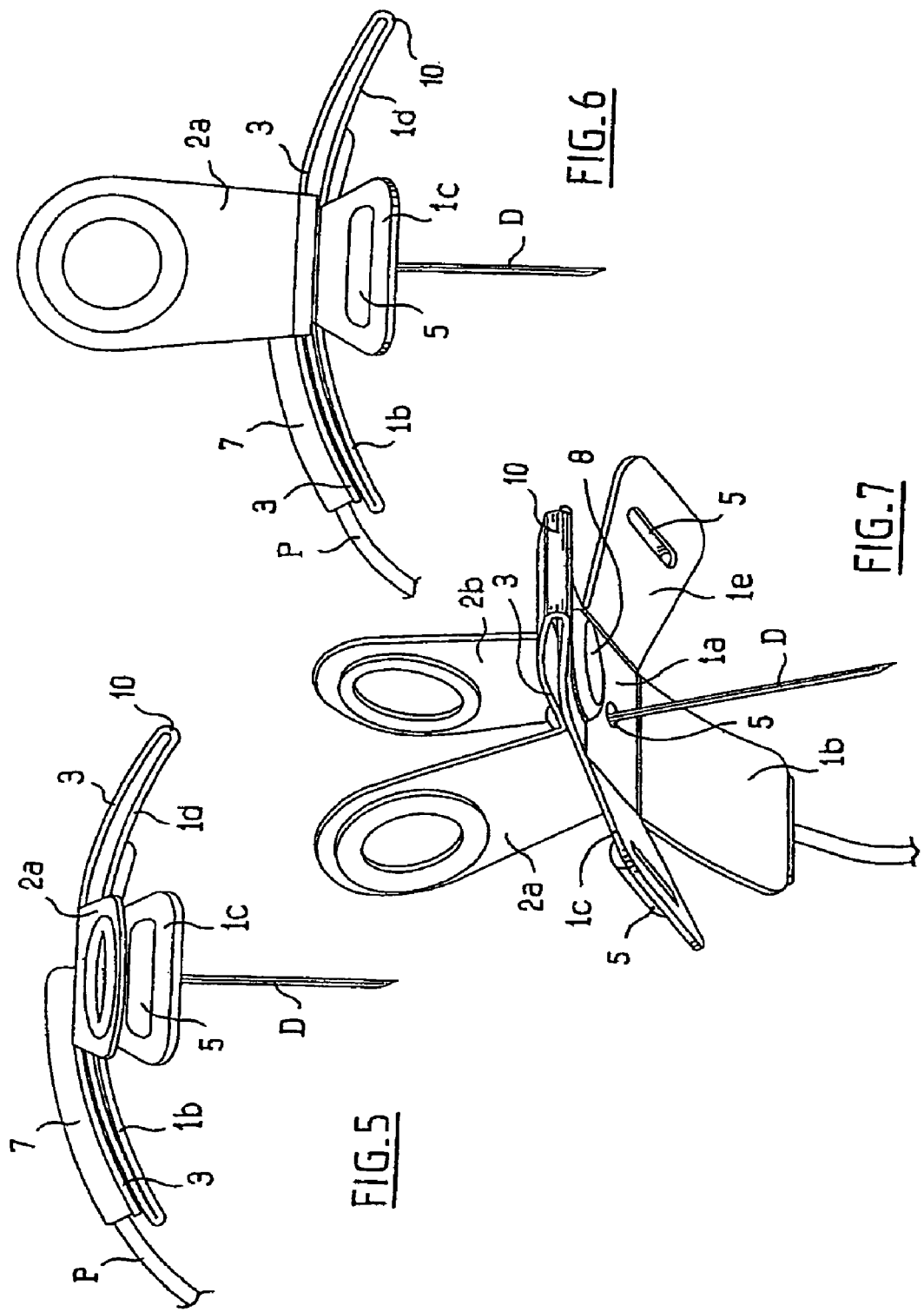

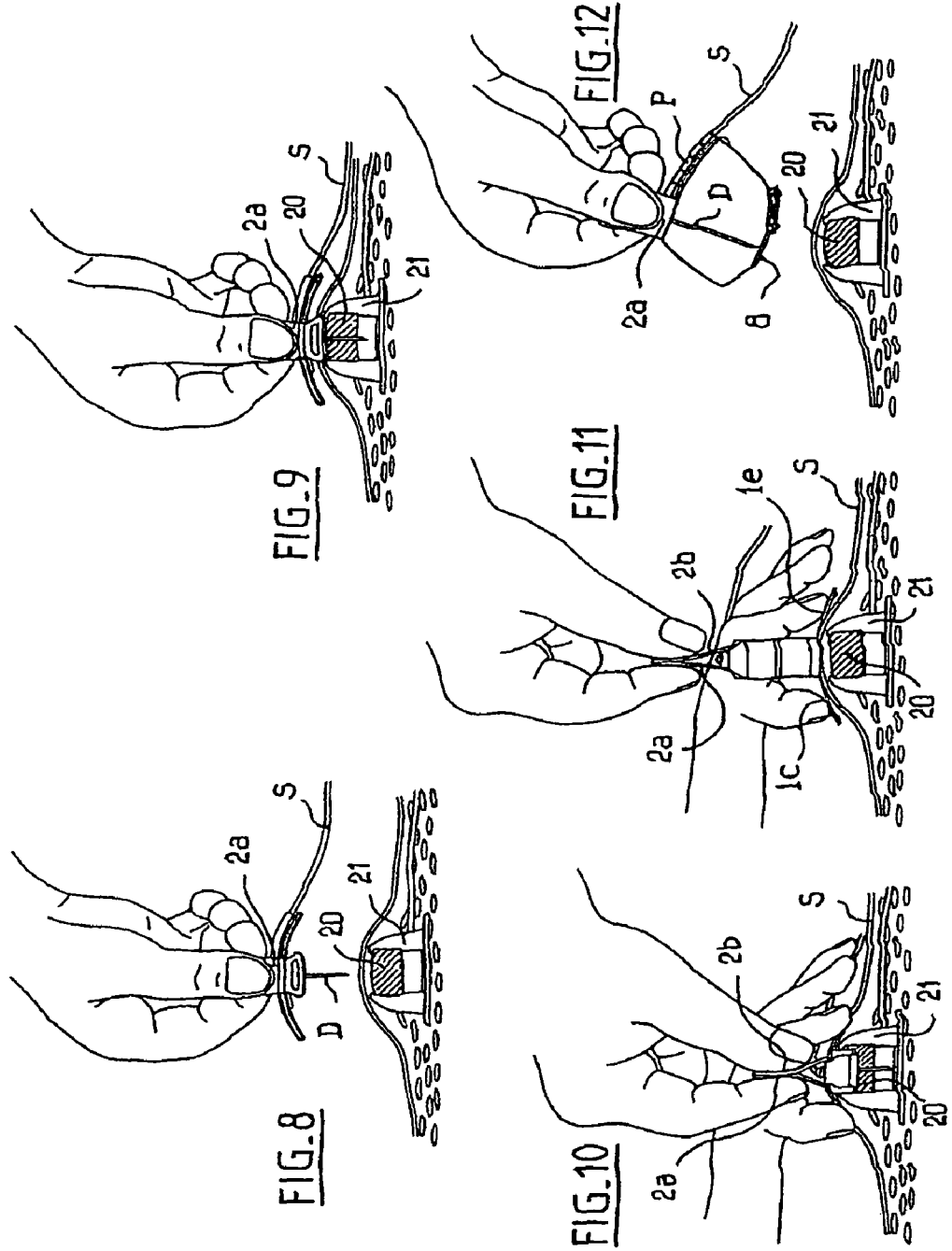

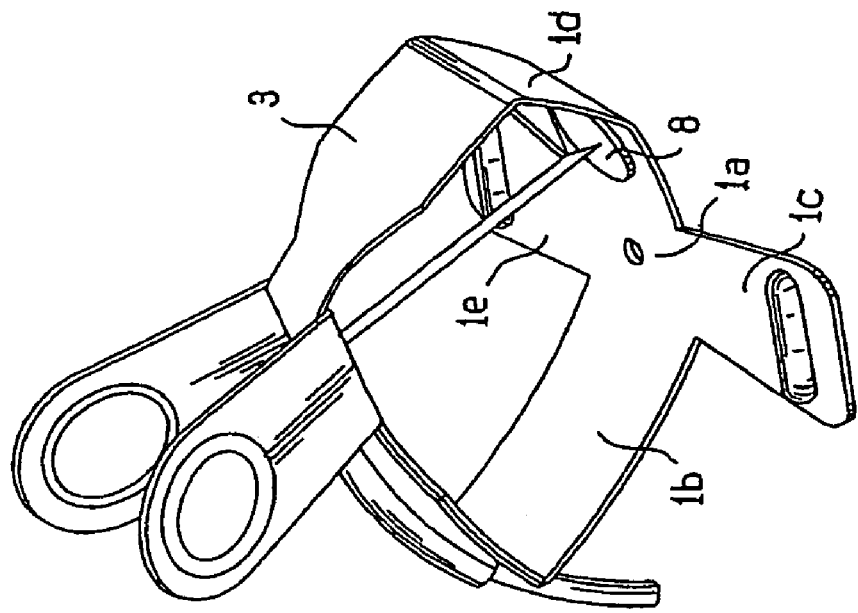
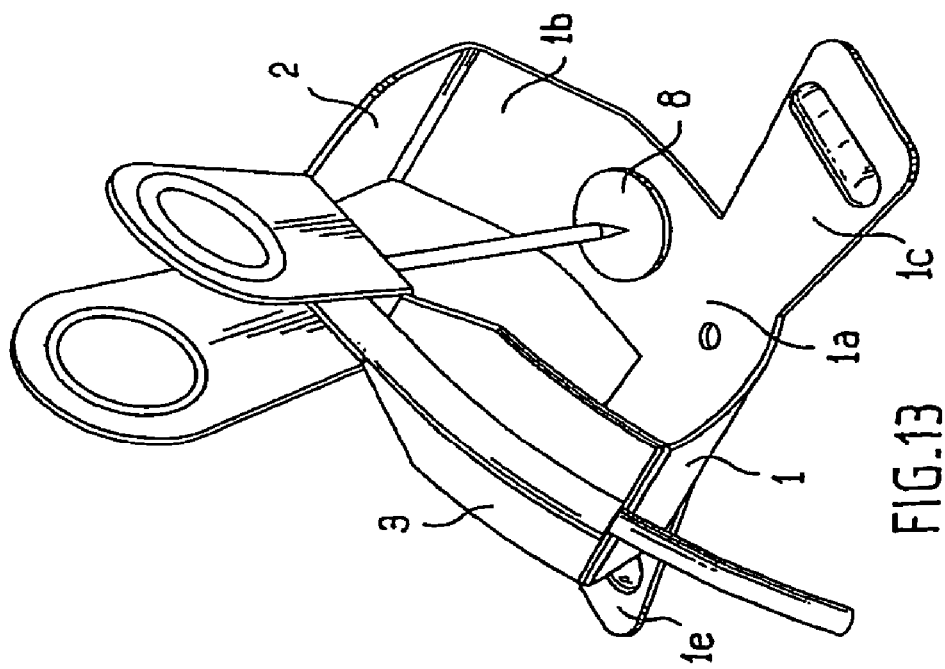

ANTI-STICK DEVICE FOR BENT INJECTION NEEDLE

The invention relates to an anti-stick device for safely maneuvering an injection needle through the skin, this needle being bent and having a perforating distal branch and a proximal feed branch which forms a bend with the perforating branch (Huber needle).

Examples of an anti-stick device for this type of needle are described in the publication FR 2 803 529 and in U.S. Pat. No. 5,951,522.

The device described in the publication FR 2 803 529 is composed of a wall formed by articulated panels which allow the wall to be brought into a configuration in which one of the panels (or needle-holding panel) is folded down onto another panel (or base panel) and in which a third panel (or covering panel) is folded down onto the needle-holding panel and fixed to it, and to be brought into a configuration in which the needle-holding panel and the covering panel fixed to one another are distanced from the base panel and form, between themselves and said base panel, a space which is sufficient to contain the distal branch of the needle, the base panel and the needle-holding panel having respective holes which permit passage of the distal branch of the needle and which coincide when the panels are applied to one another, in such a way that the distal branch can be introduced into the holes of the panels folded down one on top of the other until the proximal branch of the needle rests on the needle-holding panel, the covering panel being able to cover the proximal branch of the needle when it is folded down onto the needle-holding panel, the base panel determining a central zone including said hole in the panel and four lateral branches lying opposite one another in pairs and perpendicular to one another in pairs, and the needle-holding panel forming two lateral lugs which can be lifted to permit manual gripping of the device at the time of puncture and at the time of withdrawal of the needle.

The present invention concerns an embodiment of this device specially designed for perfusion of a chamber implanted under the skin. In this case, the needle has to pass through a septum in the form of a silicone disk situated at the summit of the incurved dome of the chamber. The device must ensure good automatic closure of the septum upon withdrawal of the needle. By way of example, it must be possible to perform 3500 punctures in a septum measuring 1.3 $cm^2$ and 3500 punctures in a septum measuring 0.63 $cm^2$. In view of the above, the needle has to be pushed very strongly during the puncturing procedure and has to be pulled very strongly when being withdrawn. This pulling during withdrawal requires the user to place two fingers on the patient's skin on each side of the needle in order to hold the implantable chamber in place. However, in view of the considerable force, rebound phenomena may occur, which may lead to the operator sustaining a needlestick injury.

The subject of the invention is a simple and inexpensive design of the device defined above, allowing the needle to be pushed in firmly and allowing it to be withdrawn firmly, without any risk of the operator sustaining a needlestick injury.

The realization of the invention is characterized in particular in that the central panel is manufactured in such a shape that two opposite lateral branches of this panel have a curvature facilitating application of these branches on the skin in line with the implanted chamber, and such that the two other opposite branches of the panel are capable of being bent at will under the pressure exerted by two fingers of a hand in order to press these branches onto the skin so as to hold the implanted chamber in place when the operator withdraws the needle with his other hand, and in that the needle-holding panel and the covering panel are contiguous, respectively, with one or other of the pre-curved branches of the base panel and have, from manufacture, a curvature which is the opposite of the curvature of said branches so as to match the curvature of the branches when they are folded down onto the base panel.

An example of such an embodiment will be described below with reference to the figures of the attached drawing, in which:

FIGS. 3 and 4 are a plan view and bottom view, respectively, of the device after the covering panel has been folded down and glued;

FIGS. 5 and 6 are perspective side views of the device, respectively before and after straightening of the grip tabs;

FIG. 7 is a perspective view of the device ready for use;

FIGS. 8 through 12 show successive phases of the operations of puncturing and withdrawal of the needle, and FIGS. 13 and 14 are perspective views of the device, seen at two angles, after withdrawal of the needle.

Figure 1:
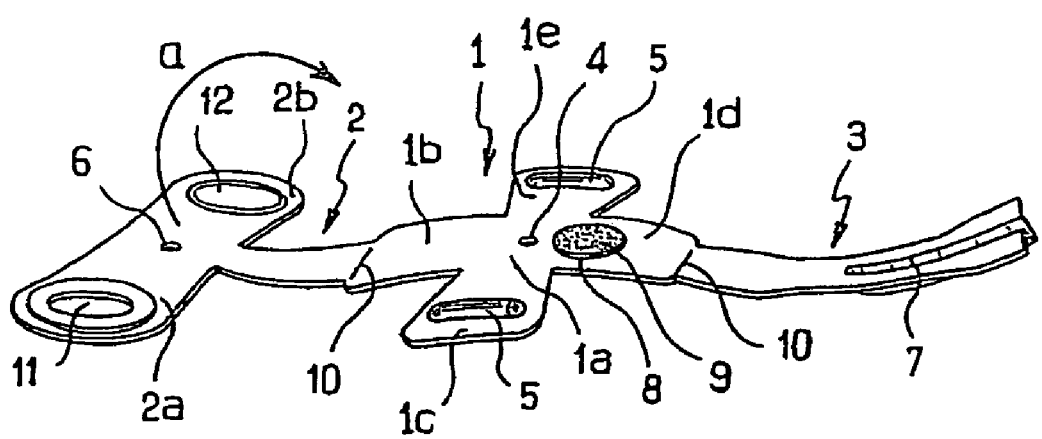
FIG. 1 is a view of the device laid flat, before folding and positioning of the needle.

The device is composed of a wall which has been cut out from a sheet of flexible and preformed plastic material.

The sheet defines (FIG. 1):

- a cross-shaped base panel (1) which comprises a central zone (1*a*) and four arms (1*b*, 1*c*, 1*d*, 1*e*) lying opposite one another in pairs and perpendicular to one another in pairs, and radiating around the central zone;
- a needle-holding panel (2) which continues the arm (1*b*) of the base panel and is hinged thereon via a fold line (10);
- a covering panel (3) which continues the arm (1*d*) of the base panel and is hinged thereon via a fold line (10).

The central zone (1*a*) of the base panel has a hole (4) for passage of the beveled distal branch (D) of a needle bent at right angles (Huber needle).

The arms (1*b*, 1*d*) of the base panel have a pre-formed curvature chosen such that the panel can match the shape of the dome of an implanted chamber.

The arms (1*c*, 1*e*) of the base panel are bendable so that they can be applied onto the skin above the dome by manual pressure. These arms advantageously have reliefs (5) to facilitate application of the operator's fingers.

The needle-holding panel (2) and the covering panel (3) are pre-formed with a curvature opposite to that of the arms (1*b*, 1*d*) so that these panels match these arms when they are folded down onto the central panel.

The needle-holding panel (2) has a hole (6) for passage of the beveled distal branch (D) of the bent needle, forms a channel (7) for receiving the proximal branch (P) of the needle and comprises two lugs (2*a*, 2*b*) which can be lifted to allow the device to be gripped.

The channel obtained by deformation of the sheet matches the curvature of the covering panel. It serves to cover the connecting zone between the two branches of the needle, the proximal branch (P) of the needle and the distal end of the flexible tube (S) which continues the needle.

It serves in addition as a reservoir for adhesive.

Near the hole (4), the base panel (1) is equipped with a disk (8) which is made of hard plastic and fitted in an aperture of the panel and whose surface has a suitable relief (9), for example striations or a grid pattern, to hold the beveled tip of the needle when this tip has been brought into contact with this surface after withdrawal of the distal branch of the needle inside the device.

The hinge folds (10) between the panels are formed by local thinning of the wall.

The lugs (2a, 2b) of the needle-holding panel are advantageously equipped with means, for example a relief (11) and a hollow (12), which can cooperate to keep the two tabs applied against one another, when this is desirable in order to avoid slipping of one tab relative to the other.

The device is supplied to the user in a (sterile) pouch in which the sheet is laid flat, the panels being substantially as shown in FIG. 1. The pouch can also contain the needle, the distal branch of which is temporarily protected by a removable cap.

Figure 2:
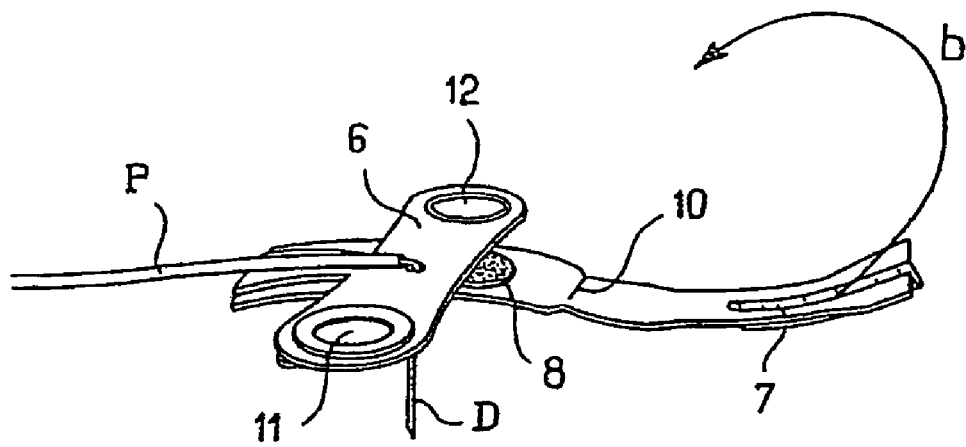
FIG. 2 is a view of the device after positioning of the needle and before the covering panel is folded down and glued to the needle-holding panel.

For using it, the device is manipulated in the following way:
- the needle-holding panel (2) is folded down onto the base panel (1), and the distal branch (D) is introduced into the superposed holes (5, 6) of the two panels (FIG. 2);
- adhesive is placed in the channel, and the covering panel (3) is folded down onto the needle-holding panel (2) so that the channel (7) covers the proximal branch (P) of the needle;
- the lugs (2a, 2b) of the needle-holding panel are lifted (FIGS. 6 and 7);
- the device is gripped between two fingers of a hand by way of the two lugs pressed against one another (FIG. 8);
- the skin is punctured in line with the dome (20) of the implanted chamber (21) with a force sufficient to ensure that the tip of the needle penetrates with force into the chamber (FIG. 9);
- the lugs are folded down onto the skin, and the device is held in place by means of a dressing or similar, for filling of the chamber.

To withdraw the needle after the chamber has been filled, the operator lifts the lugs of the device, grips them and presses with his other hand on the panels (1c, 1e) which, because of their curvature, are applied to the skin at the site of the implanted chamber so as to hold the implanted chamber in place while he withdraws the needle (FIGS. 10 and 11) by pulling on the tabs.

The central part (1a) of the panel lifts and adopts an opposite curvature. This is made possible by the cross-shaped profile of the panel and by the panel being hinged on the two other panels.

The upper part of the device curves strongly in the front area, but the rear area cannot curve because it is made rigid by the adhesive and the distal branch of the needle. All of this means it is possible to create, elastically, between the lower part and the upper part of the device, a space into which the distal branch of the needle can retract.

As the two branches of the needle rise, the initial angle of approximately 90° decreases. Thus, upon complete disengagement of the distal branch of the needle, the latter relaxes in the front area and comes to lie in the disk.

The elasticity of the deformation of the two parts (lower and upper) and the raised grid pattern of the disk prevent any rearward return, any displacement of the distal branch of the needle and, of course, any risk of needlestick injury or of reuse of the needle.

FIGS. 12 and 13 show the needle in abutment against the hard disk (8) inside the device.

The invention is not limited to this example of an embodiment according to the invention.

The invention claimed is:

1. An anti-stick device for safely maneuvering an injection needle through the skin for feeding a chamber implanted under the skin, said needle being bent and having a perforating distal branch and a proximal feed branch which forms a bend with the perforating branch, said device comprising a needle-holding panel, a base panel, and a covering panel forming a wall, said panels allowing said wall to be brought into a configuration in which said needle-holding panel is folded down onto said base panel and in which said covering panel is folded down onto said needle-holding panel and fixed thereto, and to be brought into a configuration in which said needle-holding panel and said covering panel are fixed to one another and are spaced from said base panel and form, between themselves and said base panel, a space which is sufficient to contain said distal branch of said needle, said base panel and said needle-holding panel having respective holes which permit passage of said distal branch of said needle and which coincide when said panels are joined, whereby said distal branch can be introduced into said holes until said proximal branch of said needle rests on said needle-holding panel, said covering panel covering said proximal branch of said needle when said covering panel is folded down onto said needle-holding panel, said base panel having a central zone surrounding said hole of said base panel and four lateral branches lying opposite one another in pairs and perpendicular to one another in pairs, said needle-holding panel comprising two lateral lugs which can be lifted to permit manual gripping of said device at the time of puncture and at the time of withdrawal of said needle, said base panel comprising a first pair of opposite lateral branches having a curvature for matching a contour of said base panel to a top of said chamber for application of said base panel on the skin in line with said implanted chamber, and a second pair of opposite lateral branches of said base panel capable of being bent by two fingers of one hand in order to press said second pair of branches toward the skin and said chamber for holding said chamber in place when the operator withdraws said needle, said needle-holding panel and said covering panel being contiguous, respectively, with said first pair of branches of said base panel and having a curvature which is the opposite of the curvature of said first pair of branches so as to match the curvature of said first pair of branches when they are folded down onto said base panel, wherein said device further comprises a disk of very hard plastic material attached to and fixed on one of said first pair of branches of said base panel, said disk having a relief for preventing slipping of a tip of said needle when said tip is brought into contact with said disk after retraction of said needle into said device.

2. The device as claimed in claim 1, wherein opposite branches of said second pair of branches of said base panel have reliefs for facilitating application of fingers to said second pair of branches.

3. The device as claimed in claims 1, in which said lugs of said needle-holding panel comprise means which cooperate for selectively keeping said two lugs applied against one another.

4. The device as claimed in claims 1, in which said covering panel is shaped to constitute a channel able to receive an adhesive and to cover said proximal branch of said needle when said covering panel is applied to said needle-holding panel.

5. The device as claimed in claim 1, in which said wall comprises a sheet of flexible plastic material which has been cut out and pre-formed.

6. The device as claimed in claim 1, comprising a pouch in which the wall is laid substantially flat.

7. The device as claimed in claim 6 further comprising, inside the pouch, the needle and a cap for shielding the beveled edge of the needle.

\* \* \* \* \*